(12) United States Patent
Chen et al.

(10) Patent No.: US 9,816,911 B2
(45) Date of Patent: Nov. 14, 2017

(54) FLOW CYTOMETRY OPTICS

(71) Applicant: Beckman Coulter, Inc., Brea, CA (US)

(72) Inventors: Antao Chen, Palmetto Bay, FL (US); Juan J. Fernandez De Castro, Miami, FL (US); Paul K. Church, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 35 days.

(21) Appl. No.: 15/036,712

(22) PCT Filed: Nov. 14, 2014

(86) PCT No.: PCT/US2014/065821
§ 371 (c)(1),
(2) Date: May 13, 2016

(87) PCT Pub. No.: WO2015/073911
PCT Pub. Date: May 21, 2015

(65) Prior Publication Data
US 2016/0290915 A1    Oct. 6, 2016

Related U.S. Application Data

(60) Provisional application No. 61/904,290, filed on Nov. 14, 2013.

(51) Int. Cl.
*G01N 21/25* (2006.01)
*G01N 15/14* (2006.01)
(Continued)

(52) U.S. Cl.
CPC ..... *G01N 15/1436* (2013.01); *G01N 15/1459* (2013.01); *G01N 21/53* (2013.01); *G01N 21/645* (2013.01); *G01N 2015/0065* (2013.01); *G01N 2021/6421* (2013.01); *G01N 2021/6463* (2013.01); *G01N 2021/6478* (2013.01); *G01N 2021/6484* (2013.01); *G01N 2201/0637* (2013.01)

(58) Field of Classification Search
USPC ...... 422/73, 82.07, 82.08; 356/39, 317, 417; 250/458.1
See application file for complete search history.

(56) References Cited

U.S. PATENT DOCUMENTS 6,953,252 B2 * 10/2005 Way ..................... G02B 6/0023
349/5

* cited by examiner

*Primary Examiner* — Abdullahi Nur
(74) *Attorney, Agent, or Firm* — K&L Gates LLP; Louis C. Cullman; Robert W. Winn

(57) ABSTRACT

High numerical aperture collection optics for particle analyzers may include an ellipsoidal reflector or an ellipsoidal reflector in combination with a spherical reflector, and may efficiently collect light scattered or emitted by particles in a sample stream and then couple that collected light into a lower numerical aperture portion of the instrument's optical detection system, such as into an optical fiber for example. The reflectors may be integrated with a flow cell through which the sample stream passes, or may be separate components arranged around a flow cell or, in instruments not employing a flow cell, arranged around a sample stream in air. Refractive beam steering optics may allow multiple closely spaced excitation beams to be directed into the sample stream at low angles of incidence. The collection optics and refractive beam steering optics may be employed separately or in combination with each other.

20 Claims, 7 Drawing Sheets

(51) Int. Cl.
*G01N 21/53* (2006.01)
*G01N 21/64* (2006.01)
*G01N 15/00* (2006.01)

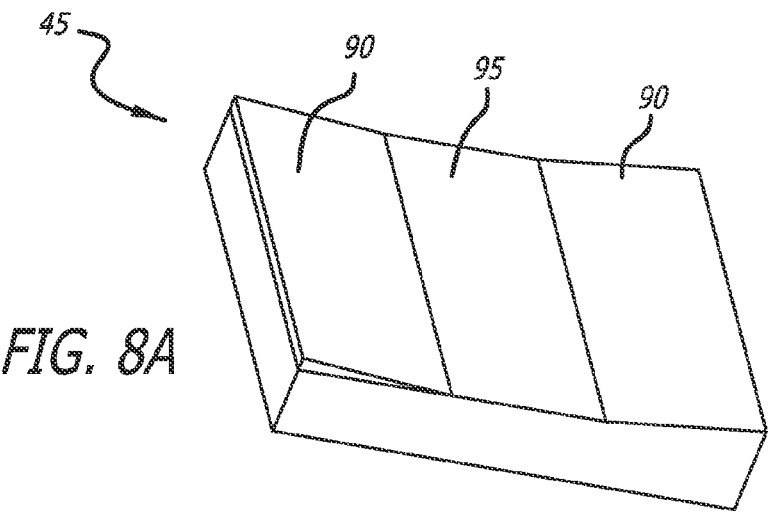
FIG. 8A
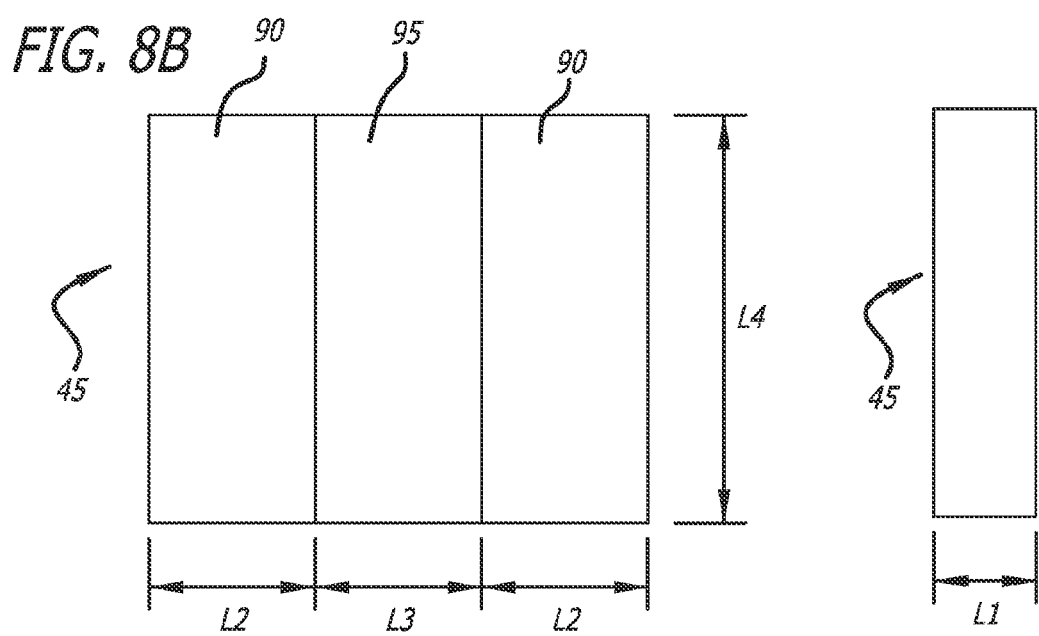
FIG. 8B
FIG. 8C
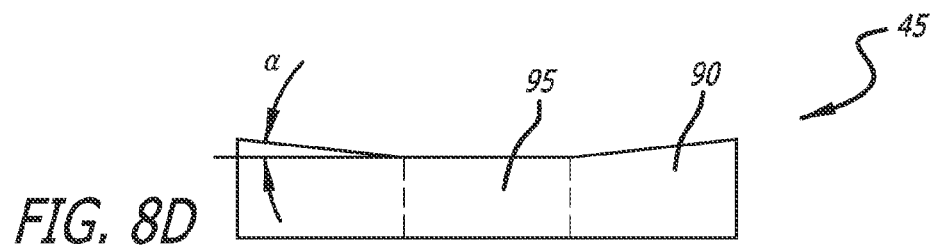
FIG. 8D

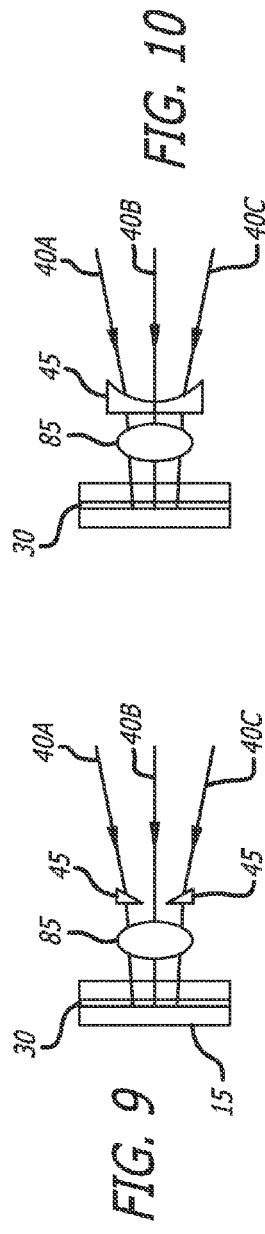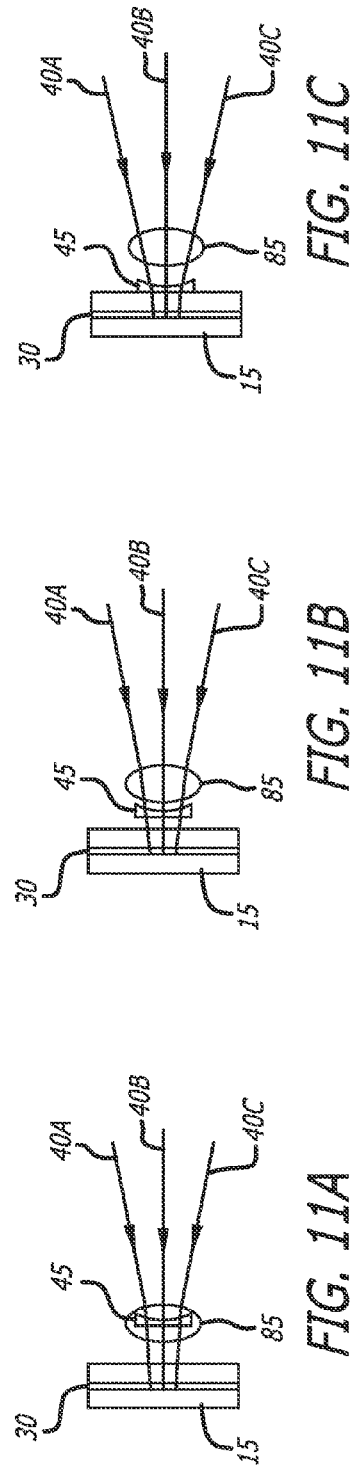

FLOW CYTOMETRY OPTICS

CROSS REFERENCE TO RELATED APPLICATIONS

This application claims priority under 35 U.S.C. §371 to International Patent Application PCT/US2014/065821, filed Nov. 14, 2014, which claims the benefit of U.S. Provisional Application No. 61/904,290, filed on Nov. 14, 2013, the disclosures of both of which are incorporated herein by reference in their entireties.

FIELD OF THE INVENTION

The invention relates generally to optical configurations and methods useful in particle analyzers and particle analysis, and more particularly to flow cytometers and flow cytometry employing such optical configurations and methods.

BACKGROUND

In flow cytometry particles such as cells, arranged in a sample stream, pass typically one-by-one through one or more excitation light beams with which the particles interact. Light scattered or emitted by the particles upon interaction with the one or more excitation beams is collected, detected, and analyzed to characterize and differentiate the particles. For example, forward scattering of an excitation beam along its axis may provide information about particle size, side scattering of an excitation beam orthogonally to its axis may provide information about particle internal structure or internal complexity, and fluorescence excited by the one or more excitation beams may provide information about the presence or absence in the particles of fluorophores correlating with particular chemical or biological properties of the particles.

In a sorting flow cytometer particles may be extracted out of the sample stream after having been characterized by their interaction with the one or more excitation beams, and thereby sorted into different groups. Such sorting may utilize, for example, gas jets, electrostatic forces, or other methods to displace selected particles from a sample stream flowing in air.

The performance of flow cytometers may be limited, for example, by the efficiency with which they collect light scattered or emitted by the particles, by susceptibility to misalignment of the their optical components, and by the difficulty with which optical components such as light sources or light detectors, for example, may be replaced or substituted without significantly misaligning or otherwise disrupting the operation of the instrument.

SUMMARY

Optical arrangements and corresponding methods that may be advantageously employed in flow cytometers and related particle analyzers are disclosed.

In one aspect, a particle analyzer comprises an ellipsoidal reflector having a shape characterized by lengths of major and minor axes of a defining ellipse and having conjugate foci F1 and F2 located on the major axis, with F1 in a flow path for a stream of particles. The particle analyzer also comprises one or more light sources configured to provide one or more excitation light beams that are directed to intersect the stream of particles at or approximately at F1, thereby exciting fluorescence from the particles, and a spherical reflector having its center of curvature coincident or approximately coincident with F1. The spherical reflector may be positioned, for example, on the opposite side of F1 from the ellipsoidal reflector. Fluorescence emitted toward the ellipsoidal reflector is focused by the ellipsoidal reflector to one or more locations at or near F2. Fluorescence emitted toward the spherical reflector is retro-reflected by the spherical reflector toward the ellipsoidal reflector, which focuses the retro-reflected fluorescence to the one or more locations at or near F2. The ratio of the major and minor axes of the ellipse defining the shape of the ellipsoidal reflector is greater than or equal to about 1.2.

The radius of curvature of the spherical reflector may be equal or approximately equal to the distance between F1 and F2. Alternatively, the radius of curvature of the spherical reflector may be less than the distance between F1 and F2, with the ellipsoidal reflector focusing fluorescence incident on it through a central portion of the spherical reflector to F2 beyond the spherical reflector.

The numerical aperture of the ellipsoidal reflector for collection of fluorescence emitted toward it may be greater than or equal to about 1.3, for example.

The ratio of the lengths of the major and minor axes of the defining ellipse may provide an ellipsoidal reflector shape that matches or approximately matches the fluorescence it focuses to locations at or near F2 to a lower numerical aperture portion of the particle analyzer. For example, the focused fluorescence may be matched to the numerical aperture of an optical fiber into which it is coupled.

The particle analyzer may comprise a flow cell formed from a material transparent or substantially transparent to light at wavelengths of the excitation beam and wavelengths of the fluorescence, and having a flow channel accommodating flow of the stream of particles along the flow path. The ellipsoidal and spherical reflectors may be integral parts of such a flow cell formed by reflective coatings on outer surfaces of the flow cell. Alternatively, the particle analyzer may lack a flow cell and the ellipsoidal and spherical reflectors may be arranged around a sample stream in air.

In another aspect, a particle analyzer comprises an ellipsoidal reflector having a shape characterized by lengths of major and minor axes of a defining ellipse and having conjugate foci F1 and F2 located on the major axis, with F1 in a flow path for a stream of particles. The particle analyzer also comprises one or more light sources configured to provide one or more excitation light beams that: are directed to intersect a stream of particles at or approximately at F1, thereby exciting fluorescence from the particles, and a spherical reflector having its center of curvature coincident or approximately coincident with F1. The spherical reflector may be positioned, for example, on the opposite side of F1 from the ellipsoidal reflector. Fluorescence emitted toward the ellipsoidal reflector is focused by the ellipsoidal reflector to one or more locations at or near F2. Fluorescence emitted toward the spherical reflector is retro-reflected by the spherical reflector toward the ellipsoidal reflector which focuses the retro-reflected fluorescence to the one or more locations at or near F2. The radius of curvature of the spherical reflector is less than the distance between F1 and F2, and the ellipsoidal reflector focuses fluorescence incident on it through a central portion of the spherical reflector to F2 beyond the spherical reflector.

The numerical aperture of the ellipsoidal reflector for collection of fluorescence emitted toward it may be greater than or equal to about 1.3, for example.

The ratio of the lengths of the major and minor axes of the defining ellipse may provide an ellipsoidal reflector shape that matches or approximately matches the fluorescence it focuses to locations at or near F2 to a lower numerical aperture portion of the particle analyzer. For example, the focused fluorescence may be matched to the numerical aperture of an optical fiber into which it is coupled.

The particle analyzer may comprise a flow cell formed from a material transparent or substantially transparent to light at wavelengths of the excitation beam and wavelengths of the fluorescence, and having a flow channel accommodating flow of the stream of particles along the flow path. The ellipsoidal and spherical reflectors may be integral parts of the flow cell formed by reflective coatings on outer surfaces of the flow cell. Alternatively, the particle analyzer may lack a flow cell and the ellipsoidal and spherical reflectors may be arranged around a sample stream in air.

In another aspect, a particle analyzer comprises a flow cell comprising a flow channel accommodating flow of a stream of particles, and an ellipsoidal reflector having a shape characterized by lengths of major and minor axes of a defining ellipse and having conjugate foci F1 and F2. The ellipsoidal reflector is formed as an integral part of the flow cell by a reflective coating on an exterior surface of the flow cell with F1 in the flow channel. The flow cell extends along the major axis of the defining ellipse to an end surface at or approximately at F2. The particle analyzer also comprises one or more light sources configured to provide one or more excitation light beams that are directed to intersect the stream of particles at or approximately at F1, thereby exciting fluorescence from the particles, and one or more optical fibers bonded to the end surface of the flow cell at or approximately at F2. Fluorescence excited by the one or more excitation beams and emitted toward the ellipsoidal reflector is focused by the ellipsoidal reflector to one or more locations at or near F2 and thereby coupled into the one or more optical fibers. The ratio of the lengths of the major and minor axes of the defining ellipse provide an ellipsoidal reflector shape that matches or approximately matches the fluorescence focused to locations at or near F2 to the numerical aperture of at least one of the one or more optical fibers.

The numerical aperture of the ellipsoidal reflector for collection of fluorescence emitted toward it may be greater than or equal to about 1.3, for example. The ratio of the lengths of the major and minor axes may be greater than or equal to about 1.4, for example.

In another aspect, a particle analyzer comprises collection optics arranged to collect light scattered or emitted from a sample stream of particles and direct the collected light to one or more light detectors. The particle analyzer also comprises three or more excitation light sources each providing an excitation beam of light, and a refractive beam steering optic which directs the three or more excitation beams to intersect the sample stream at corresponding separate and spaced-apart locations along the sample stream. Excitation beams passing through opposite outer portions of the refractive beam steering optic are deflected away from each other to thereby reduce their angles of incidence on the sample stream.

The refractive beam steering optic may direct each of the excitation beams into the sample stream at an angle of incidence less than or equal to about 1 degree, for example.

The refractive beam steering optic may, for example, be a single integrated optical element comprising at least two outer wedge portions arranged symmetrically around a central flat portion. The excitation beam paths may be arranged in this case so that at least one of the excitation beams is incident on and passes substantially undeflected through the central flat portion to the sample stream, and excitation beams incident on wedge portions on opposite sides of the central flat portion are deflected away from each other to redirect them toward the sample stream at reduced angles of incidence.

The refractive beam steering optic may alternatively comprise at least two separate optical wedges arranged symmetrically around an air gap. The excitation beam paths may be arranged in this case so that at least one of the excitation beams passes undeflected through the central air gap to the sample stream, and excitation beams incident on wedges on opposite sides of the air gap are deflected away from each other to redirect them toward the sample stream at reduced angles of incidence.

The refractive beam steering optic may alternatively comprise a diverging cylindrical lens. The excitation beam paths may be arranged in this case so that at least one of the excitation beams passes substantially undeflected through a central portion of the cylindrical lens to the sample stream, and excitation beams incident on opposite outer portions of the cylindrical lens are deflected away from each other to redirect them toward the sample stream at reduced angles of incidence.

The collection optics may comprise, for example, an ellipsoidal reflector having a focus located in the sample stream among the locations intersected by the excitation beams, and a spherical reflector having a center of curvature coincident or approximately coincident with that focus of the ellipsoidal reflector.

In another aspect, a particle analyzer comprises an ellipsoidal reflector having a shape characterized by lengths of major and minor axes of a defining ellipse and having conjugate foci F1 and F2 located on the major axis, with F1 in a flow path for a stream of particles. The particle analyzer also comprises a spherical reflector having its center of curvature coincident or approximately coincident with F1. The ellipsoidal and spherical reflectors are highly reflective to one or more signals indicating the presence of a particle at or approximately at F1 and cooperate to collect and focus the one or more signals to one or more locations at or near F2. The ratio of the major and minor axes of the ellipse defining the shape of the ellipsoidal reflector may be greater than or equal to about 1.2, and/or the radius of curvature of the spherical reflector may be less than the distance between F1 and F2.

The one or more signals indicating the presence of a particle at or approximately at F1 may comprise, for example, luminescence from the particle that is excited by a beam of light intersecting the stream of particles. The signals may, for example, alternatively or in addition comprise light scattered by the particle out of a beam of light intersecting the stream of particles. The one or more signals may, for example, characterize one or more chemical, physical, or biological properties of the particle.

The particle analyzer may comprise a flow cell formed from a material transparent or substantially transparent to the one or more signals and having a flow channel accommodating flow of the stream of particles along the flow path. In such a case, the ellipsoidal and spherical reflectors may be integral parts of the flow cell formed by reflective coatings on outer surfaces of the flow cell. Except for the flow channel, all interior portions of the flow cell may, for example, be solid and formed from the transparent or substantially transparent material.

In another aspect, a flow cytometer comprises a flow cell comprising a flow channel accommodating flow of a sample stream of particles and an ellipsoidal reflector having conjugate foci F1 and F2. The ellipsoidal reflector is formed as an integral part of the flow cell by a reflective coating on an exterior surface of the flow cell with F1 in the flow channel. The flow cell extends along an axis through F1 and F2 to an end surface at or approximately at F2. The flow cytometer also comprises an optical fiber bonded to the end surface of the flow cell at or approximately at F2. The ellipsoidal reflector collects optical signals emitted from or approximately from F1 over a collection numerical aperture of about 1.1 to about 1.5 and focuses the optical signals to the optical fiber within a cone half angle not exceeding a numerical aperture of about 0.2 to about 0.5 that characterizes the optical fiber.

The optical fiber may be, for example, one of a plurality of optical fibers bonded to the end surface at or approximately at F2 and into which the ellipsoidal reflector couples optical signals emitted from or approximately from F1.

The flow cytometer may comprise a spherical reflector, also formed as an integral part of the flow cell by a reflective coating on an exterior surface of the flow cell, with its center of curvature coincident or nearly coincident with F1. In such cases the spherical reflector reflects optical signals emitted from or approximately from F1 toward the ellipsoidal reflector to be focused by the ellipsoidal reflector to the optical fiber. The radius of curvature of the spherical reflector may be, for example, equal to approximately equal to the distance between F1 and F2. Alternatively, the radius of curvature of the spherical reflector may be less than the distance between F1 and F2.

The optical arrangements and methods summarized above and described in more detail below may, for example, provide high light collection efficiencies and stable optical alignments, may facilitate replacement or modification of light sources, and may reduce system cost by reducing the total number of required components.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIGS. 8A-8D schematically illustrate cross-sectional and perspective views of the wedge lens of FIG. 7.

FIG. 9 schematically illustrates the use of two separate symmetrically arranged optical wedges as a refractive beam steering optic to direct multiple excitation laser beams into the flow cell of a flow cytometer at reduced angles of incidence on the flow stream.

FIG. 10 schematically illustrates the use of a diverging concave cylindrical lens as a refractive beam steering optic to direct multiple excitation laser beams into the flow cell of a flow cytometer at reduced angles of incidence on the flow stream.

FIGS. 11A-11E schematically illustrate five additional arrangements of the wedge lens of FIG. 7 in combination with a beam shaper (also shown in FIG. 7) that shapes the transverse profile (cross-sectional shape) of the excitation beams.

DETAILED DESCRIPTION

The following detailed description should be read with reference to the drawings, in which identical reference numbers refer to like elements throughout the different figures. The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used in this specification and the appended claims, the term parallel is intended to mean "parallel or substantially parallel" and to encompass minor deviations from parallel geometries rather than to require that arrangements described as parallel be exactly parallel. Similarly, the term perpendicular is intended to mean "perpendicular or substantially perpendicular" and to encompass minor deviations from perpendicular geometries rather than to require that arrangements described as perpendicular be exactly perpendicular.

This specification describes optical arrangements and corresponding methods that may be advantageously employed in flow cytometers and related particle analyzers to generate, collect, and/or detect indicative signals for the purpose of particle analysis. Such indicative signals may include, for example, fluorescence or other light-induced luminescence, elastically or inelastically scattered excitation light, side-scattered excitation light, or any other signal that may be useful for detecting particles and/or characterizing particle properties. These optical arrangements include high numerical aperture collection optics that may efficiently collect indicative signals such as light scattered or emitted by particles in a sample stream and then couple the collected signals (e.g., collected light) into a lower numerical aperture portion of the instrument's optical detection system, such as into an optical fiber for example. The collection optics includes, for example, an ellipsoidal reflector or an ellipsoidal reflector in combination with a spherical reflector. These reflectors may be integrated with a flow cell through which the sample stream passes, or may be separate components arranged around a flow cell or, in instruments not employing a flow cell, arranged around a sample stream in air. The optical arrangements described herein may also include refractive beam steering optics that allow multiple closely spaced excitation beams to be directed into the sample stream at low angles of incidence. As described below, these refractive beam steering optics may include, for example, a wedge lens, a pair of wedges, or a cylindrical lens.

Figure 6:
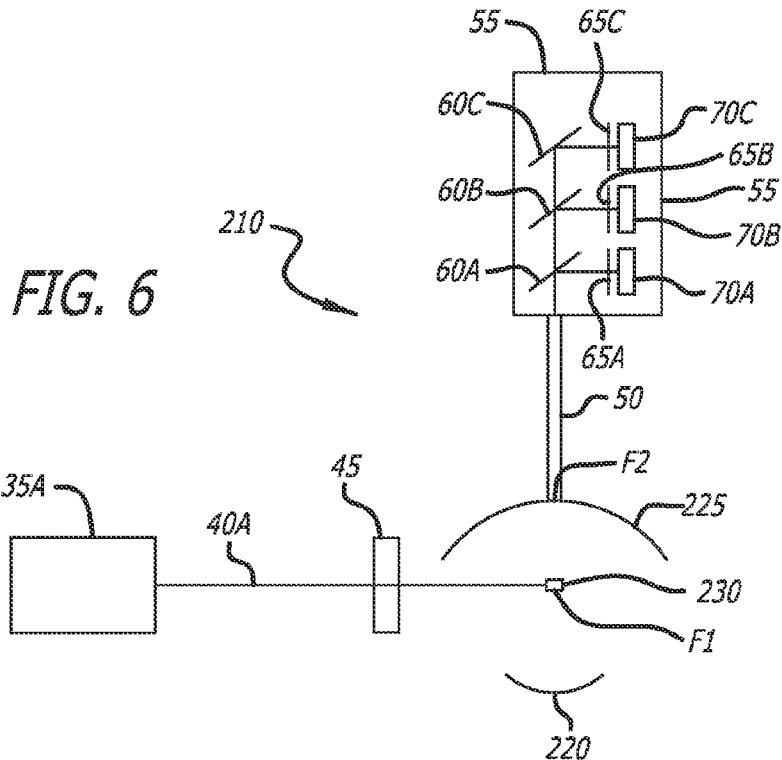
FIG. 6 schematically illustrates a top view of an example flow cytometer employing ellipsoidal and spherical reflectors to collect light scattered or emitted from a sample stream in air.

The high efficiency collection optics and the refractive beam steering optics described herein may be advantageously employed together, and FIGS. 1A-1B and FIG. 6 described in more detail below illustrate example instruments employing such a combination. However, the collection optics may also be advantageously employed in particle analyzers not including the beam steering optics, and the beam steering optics may be advantageously employed in particle analyzers not including the collection optics.

Figure 1A:
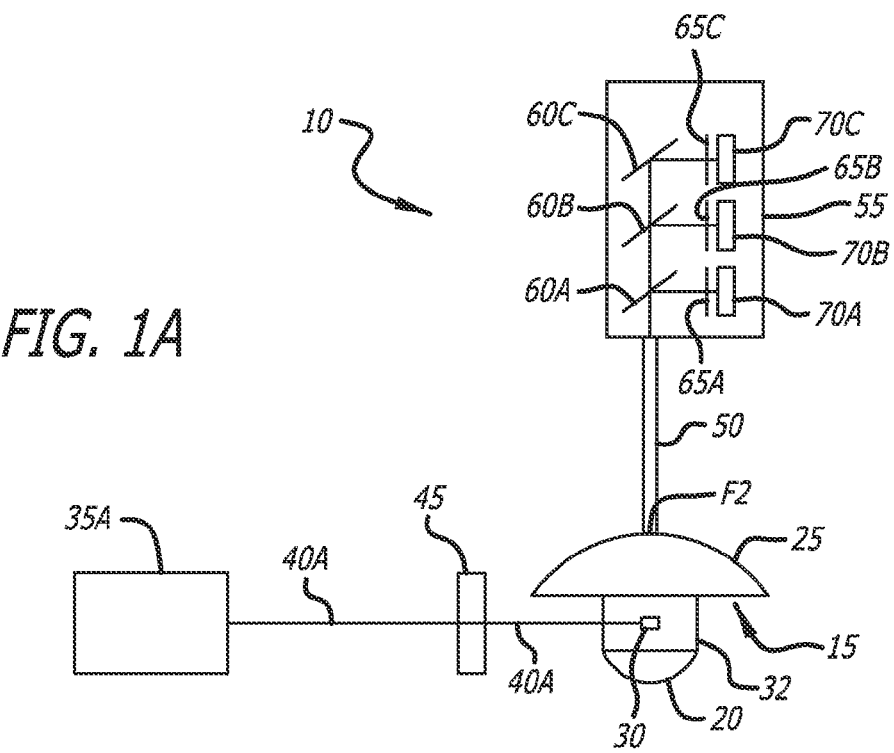
FIGS. 1A-1B schematically illustrate top and side views, respectively, of an example flow cytometer employing a flow cell comprising integrated ellipsoidal and spherical reflectors that collect light scattered or emitted from a sample stream passing through the flow cell, as well as refractive beam steering optics that allow multiple closely spaced excitation beams to be directed into the sample stream at low angles of incidence.
Figure 1B:
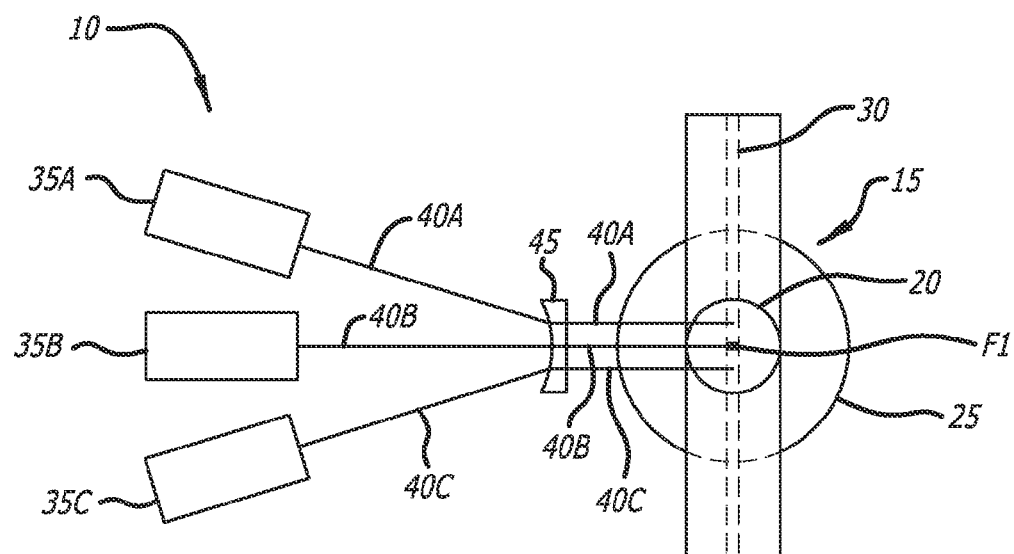

Referring now to FIG. 1A (top view) and FIG. 1B (side view), particle analyzer 10 schematically illustrated in these figures includes a flow cell 15 comprising an integrated ellipsoidal reflector 20 and an integrated spherical reflector 25. Reflectors 20 and 25 are highly reflective for light at wavelengths emitted by fluorophores located in or on the particles to be analyzed, and optionally highly reflective for light at wavelengths used by the particle analyzer to excite emission from the fluorophores. Reflectors 20 and 25 are formed by coatings deposited, respectively, on ellipsoidally and spherically shaped outer surfaces of flow cell 15. These coatings may be or comprise, for example, conventional metal or dielectric layers or stacks of such layers. In the illustrated example the interior of flow cell 15 is solid, except for a flow channel 30 passing through a central block 32 of the flow cell that is positioned between the ellipsoidal and spherical reflectors. The solid material in the interior of flow cell 15 is substantially transparent to light at the fluorphore excitation and emission wavelengths.

A sample stream of particles suspended in a liquid may be introduced into and flow through channel 30 in flow cell 15. Channel 30 may have, for example, a circular or rectangular cross section perpendicular to its long axis. The sample stream may be, for example, conventionally hydrodynamically focused in channel 30 with a core stream of particles surrounded and spatially constrained by a particle-free sheath stream, so that the particles pass essentially in-line and one by one through interaction volumes defined by the intersection of the sample stream and excitation light beams (discussed below).

Light source modules 35A-35C, typically comprising a semiconductor diode laser and collimation optics, provide excitation light beams 40A-40C. The spectrum of each excitation light beam is typically a different narrow band of wavelengths between about 405 nanometers (nm) and about 640 nm, with the wavelengths of the excitation beams selected to excite different fluorophores that may be present in or on particles in the sample stream. Excitation beams 40A-40C may have, for example, cross-sections with Gaussian radial intensity profiles having a $1/e^2$ diameter less than or equal to about 1 millimeter (mm) and a power of about 20 milliwatts (mW) to about 100 mW. Any other suitable wavelengths, beam shapes, beam diameters, and powers may also be used. Further, although the illustrated example employs three excitation beams, more or fewer excitation beams may be used as suitable. Any other suitable light sources, including lamps or other lasers, may also be used instead of or in addition to semiconductor diode lasers to provide the excitation beams.

Excitation beams 40A-40C are incident on refractive beam steering optic 45, which directs the incoming beams through an optional beam shaper (not shown) into flow cell 15 to intersect channel 30 at three spaced-apart locations along channel 30 to provide three spaced-apart interaction volumes. If present, the beam shaper typically focuses the excitation beams to elliptically shaped beam waists at channel 30, with the beam waists' minor axes oriented parallel to the channel and their major axes oriented perpendicular to the channel. Each beam waist may have, for example a $1/e^2$ diameter of about 10 microns along its minor axis and a $1/e^2$ diameter of about 60 to about 100 microns along its major axis. The spacing along channel 30 between the interaction volumes defined by the intersection of the focused excitation beams and channel 30 may be, for example, about 125 microns. The plurality of spaced-apart interaction volumes may be distributed along channel 30 over a total length, for example, of ≤about: 300 microns or ≤about 600 microns. Any other suitable interaction volume spacing and any other suitable beam waist sizes and shapes may also be used. Design details of refractive beam steering optic 45 and of the optional beam shaper are discussed below with respect to FIGS. 7-11C.

Referring now particularly to FIG. 1B, as illustrated the outer two of excitation beams 40A-40C are incident on refractive beam steering optic 45 at relatively large angles of incidence, and refractive beam steering optic 45 deflects the two outer beams away from each other to redirect them to intersect flow cell channel 30 and the sample stream at reduced angles of incidence. These reduced angles of incidence reduce the length along channel 30 of the corresponding interaction volumes. This in turn results in lower noise and higher detection sensitivity for light scattered or emitted by the particles as they transit the excitation volume, because the detection electronics may be operated with shorter acquisition time windows than would be the case for longer interaction volumes.

Referring again to both FIG. 1A and FIG. 1B, ellipsoidal reflector 20 is oriented with its major (long axis) perpendicular to channel 30 and with one (F1) of its two conjugate foci located in channel 30 among the interaction volumes defined by the intersection of the excitation beams with the sample stream. The interaction volumes are thus located approximately at F1. Each excitation volume may be located, for example, ≤about 300 microns from F1. The ellipsoidal reflector's other conjugate focus (F2) is located at or approximately at the surface of spherical reflector 25 along the major axis of the ellipsoidal reflector. Spherical reflector 25 is positioned with its center of curvature coincident or approximately coincident with focus F1 of the ellipsoidal reflector. (In this example the radius of curvature of the spherical reflector is thus equal or approximately equal to the distance between the conjugate foci of the ellipsoidal reflector).

Emission (fluorescence) from fluorophores on or in a sample particle passing through an interaction volume may be emitted substantially omnidirectionally, for example. The dimensions of the interaction volumes in channel 30 are very small compared to the ellipsoidal and spherical reflectors, so from the standpoint of the reflectors the interaction volumes are essentially point sources for light scattered or emitted by particles interacting with the excitation beams. Consequently, light emitted from an interaction volume and incident on ellipsoidal reflector 20 will be focused to a corresponding small spot at or near F2. Light emitted from an interaction volume and incident on spherical reflector 25 will be retro-reflected back through that interaction volume to ellipsoidal reflector 20, which will then focus the light to the spot at or near F2 corresponding to that interaction volume. Because the interaction volumes are spaced apart along channel 30, the ellipsoidal reflector will focus the light it collects from the interaction volumes to a corresponding arrangement of (e.g., closely spaced and possibly but not necessarily overlapping) spots at or near F2, one for each interaction volume. Flow cell 15 and its optical characteristics are further described below with respect to FIG. 2.

Still referring to FIGS. 1A-1B, light emitted from one or more of the interaction volumes in channel 30 and focused by the collection optics to a spot at or near F2 may be coupled into an optical fiber 50 that is coupled (e.g., bonded) to the spherical reflector at or near F2. Optical fiber 50 transmits the collected light to a detector module 55. In the illustrated example, detector module 55 includes dichroic beam splitters 60A-60C configured to reflect selected spectral portions of the collected light through corresponding band-pass filters 65A-65C to corresponding light detectors 70A-70C. Electrical output from the detectors may be processed by conventional detection electronics, not shown. By this arrangement, fluorescence emitted by fluorophores having different emission spectra may be separately detected by different detectors. The illustrated example employs three detectors with corresponding beam splitters and filters, but any suitable number of detectors with corresponding beam splitters and filters may be used. Further, any other suitable arrangement of spectrum-splitting optics (e.g., filters, dichroic mirrors, prisms, gratings) and detectors that provides a similar function may also be used. Detectors 70A-70C may be or comprise, for example, commercially available photomultiplier tubes (PMTs) or silicon avalanche photodiodes (Si-APDs).

The illustrated variation includes only a single optical fiber and a single detector module. In such variations, light collected from all excitation volumes may be coupled into the single fiber and transmitted to the detector module. The detector module and associated detector electronics may then distinguish light of the same wavelength originating in different interaction volumes based on the timing of the detected signals, for example. This is possible because the particles in the sample stream transit the excitation volumes in sequence, which results in a corresponding time-ordered sequence of signals from the detectors.

Alternatively, particle analyzer 10 may include two or more optical fibers 50 and associated detector modules 55. For example, some variations include a separate optical fiber for each interaction volume, with each optical fiber coupled (e.g., bonded) to the spherical reflector at or near F2 to collect light from a different one of the interaction volumes. This is possible because, as described above, light collected from the different excitation volumes may be focused at or near F2 to form a corresponding arrangement of spatially separated spots, one for each interaction volume. Each optical fiber then transmits light collected from its corresponding excitation volume to a different detector module.

FIGS. 1A-1B and the other figures discussed in the specification generally omit optical mounts or other supporting apparatus or framework that should be understood to be present to the extent necessary to maintain the various components of the illustrated devices in the illustrated arrangements. Generally, any suitable mounts, supports, or supporting frameworks may be used for this purpose.

Figure 2:
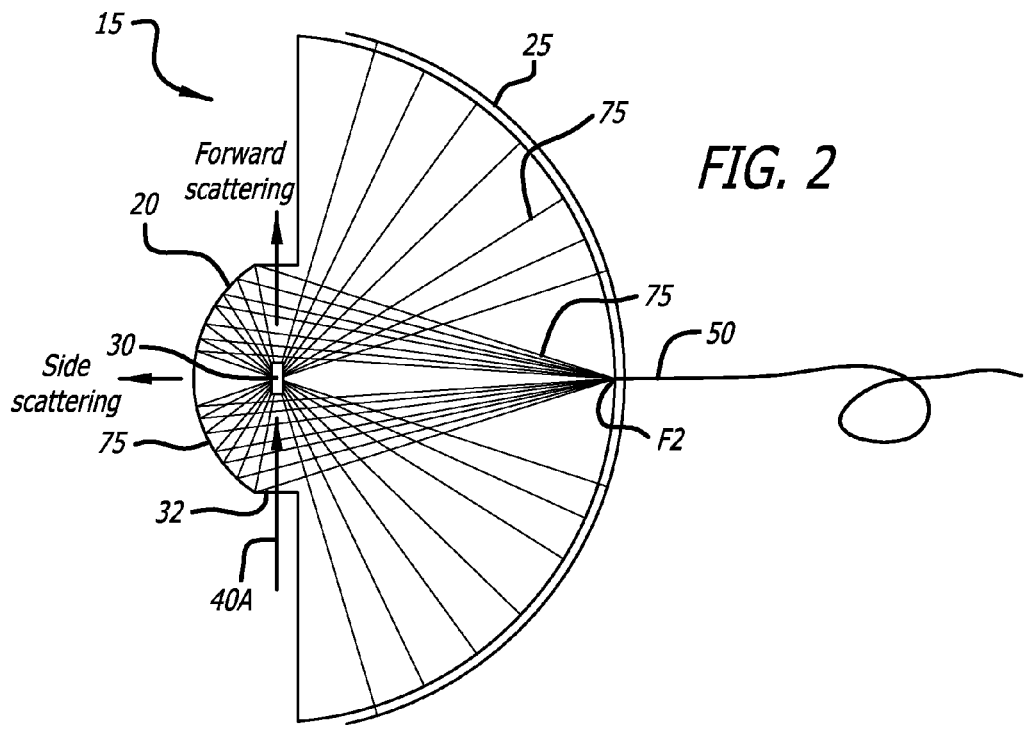
FIG. 2 schematically illustrates a cross-sectional view of an example flow cell comprising integrated ellipsoidal and spherical reflectors that may be employed in the flow cytometer of FIGS. 1A-1B.
Figure 3A:
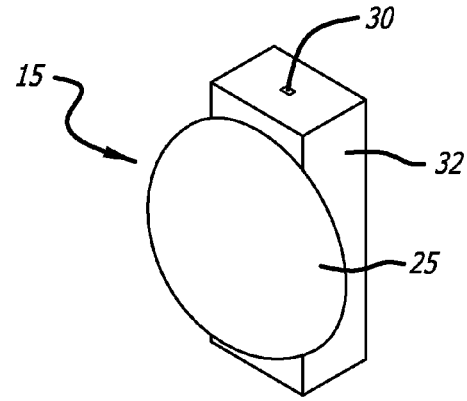
FIGS. 3A-3G show various perspective views of the flow cell of FIG. 2.
Figure 3B:
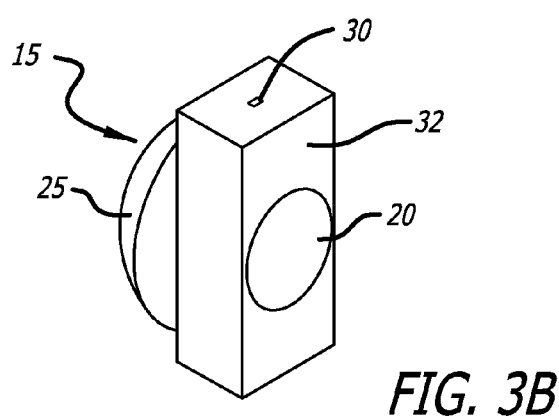
Figure 3C:
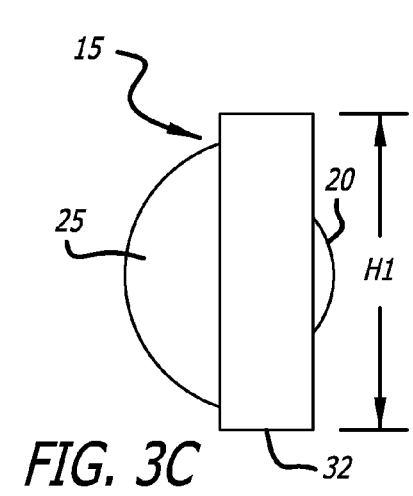
Figure 3D:
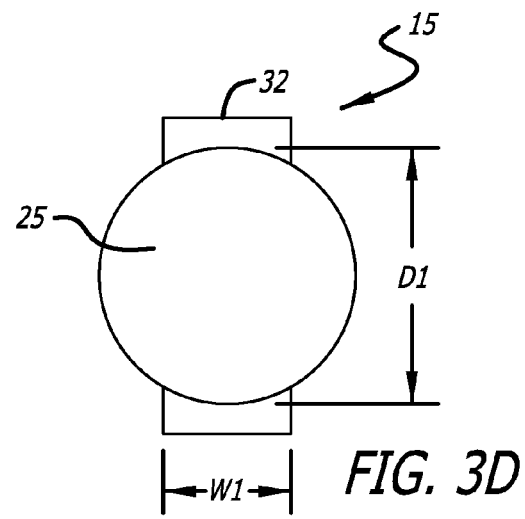
Figure 3E:
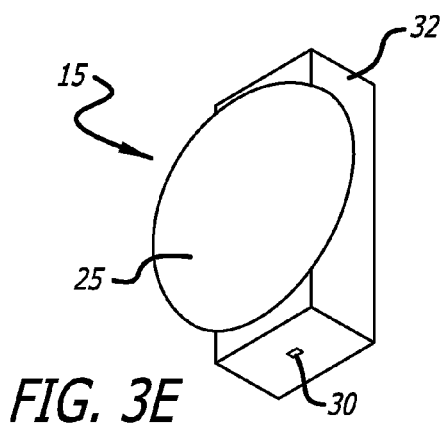
Figure 3F:
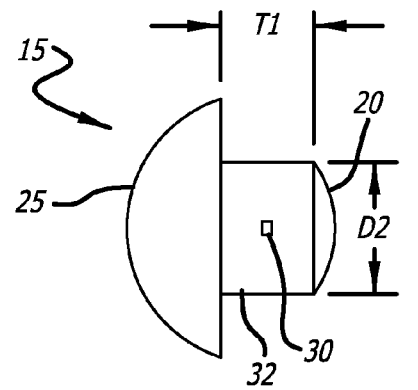
Figure 3G:
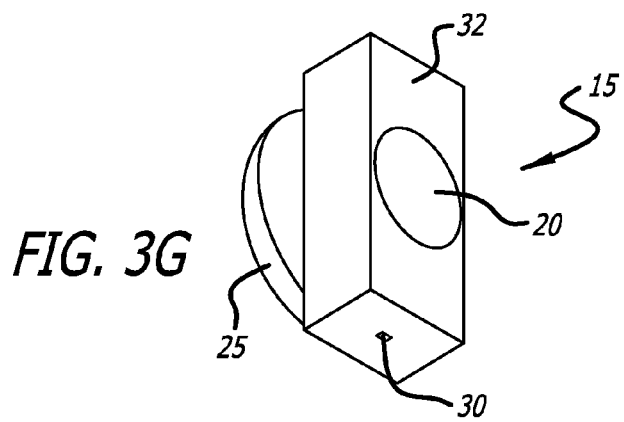

The design and optical characteristics of flow cell 15 may be better understood by reference to FIG. 2, in which light rays 75 show how, consistent with the description above, fluorescence emitted omnidirectionally from channel 30 is collected by the ellipsoidal and spherical reflectors and focused at or near F2. This figure also demonstrates that the ellipsoidal reflector may be configured to collect fluorescence over a large range of angles (i.e., provide a high numerical aperture for collection at F1) while focusing the collected light to F2 in a much smaller cone angle, which may match the relatively small numerical aperture of optical fiber 50.

Numerical aperture (NA) increases as the half angle $\theta$ of the cone of the light being collected increases. The formula for numerical aperture is $NA = n*\sin(\theta)$ where n is the index of refraction of the media the light is in. The solid substantially transparent material interior to flow cell 15 may be fused silica or other optical glasses, for example. The range of index of refraction for these materials is typically about 1.5 to about 1.7. Table 1 below tabulates the half angle $\theta$ for various values of numerical aperture and refractive index.

TABLE 1

Cone half angle as a function of NA and n.

| | NA | | | | | |
|---|---|---|---|---|---|---|
| n | 1 | 1.1 | 1.2 | 1.3 | 1.4 | 1.5 |
| 1.5 | 41.81 | 47.17 | 53.13 | 60.07 | 68.96 | 90.00 |
| 1.6 | 38.68 | 43.43 | 48.59 | 54.34 | 61.04 | 69.64 |
| 1.7 | 36.03 | 40.32 | 44.90 | 49.88 | 55.44 | 61.93 |

As Table 1 indicates, a numerical aperture of about 1.3 can be achieved with a half angle for the cone of collection around flow channel 30 of about 50 to about 60 degrees, and a numerical aperture of about 1.4 can be achieved with a half angle of about 55 to about 70 degrees. These ranges of angles can be achieved with a practical ellipsoidal mirror. Consequently, optical arrangements employing ellipsoidal reflectors as described herein may collect more light than is typical in conventional particle analyzers. This increased light collection may improve the sensitivity with which particle or particle characteristics are detected by the particle analyzer. In addition, the increased light collection may reduce the required sensitivity of the detector, allowing less expensive, more robust, and more compact Si-APDs to be substituted for PMTs.

The cone angle of the light focused by the ellipsoidal reflector to F2 is determined by the ratio of the length of the major axis of the ellipsoidal reflector to the length of the minor axis of the ellipsoidal reflector. (Note that these are parameters characterizing the shape of the ellipsoid from which the reflector is formed, not particular dimensions of flow cell 15). The larger this ratio is, the smaller the cone angle at F2. Thus the shape of the ellipsoidal reflector may be selected to match the cone of light focused at F2 to the numerical aperture of the optical fiber into which the light is coupled. Table 2 relates optical fiber NA to the ratio of the lengths of the major and minor axes of the ellipsoidal reflector for a range of example optical fiber NA's (and thus major/minor axis ratios) that may be employed in the apparatus and methods disclosed herein. In Table 2, "a" is half the length of the major axis and "b" is half the length of the minor axis. Table 2 also provides the radius of curvature Rc of the spherical reflector in flow cell 15 for the given values of "a" and "b" if F2 is located at the surface of the spherical reflector.

TABLE 2

Ellipsoidal reflector parameters to match optical fiber NA

| fiber NA | a | b | a/b | Rc |
|---|---|---|---|---|
| 0.2 | 12.72 | 7.69 | 1.65 | 20.26 |
| 0.3 | 9.05 | 6.39 | 1.42 | 12.80 |
| 0.4 | 7.21 | 5.62 | 1.28 | 9.02 |
| 0.5 | 6.11 | 5.10 | 1.20 | 6.71 |

Matching the cone of light focused to F2 to the numerical aperture of the optical fiber into which the light is coupled increases the efficiency with which light collected by the reflectors is transmitted to the detectors. (If instead of matching the numerical aperture of the optical fiber the cone of light is larger than the numerical aperture of the optical fiber, a portion of the light focused onto the optical fiber at F2 will not enter the optical fiber and thus not reach the detectors). This is another reason that optical arrangements employing ellipsoidal reflectors as described herein may improve the sensitivity with which particles or particle characteristics are detected, or allow the use of lower sensitivity detectors in place of PMTs.

The ratio of the lengths of the major and minor axes characterizing ellipsoidal reflector 20 in flow cell 15 may be, for example, $\geq 1.1$, $\geq 1.2$, $\geq 1.3$, $\geq 1.4$, $\geq 1.5$, $\geq 1.6$, or $\geq 1.7$. This ratio may be, for example, about 1.2 to about 1.7, and/or about 1.1 to about 2.0. The ratio may typically be about 1.4, for example. As noted above, the ratio of the lengths of the major and minor axes may be selected to match the cone angle of the light focused at F2 to the numerical aperture of optical fiber 50. The numerical aperture of optical fiber 50 may be, for example, $\leq 0.5$, $\leq 0.4$, $\leq 0.3$, $\leq 0.2$, or $\leq 0.1$. The numerical aperture of optical fiber 50 may be, for example, about 0.1 to about 0.5. The numerical aperture of optical fiber 50 may typically be about 0.3, for example.

The length of the major axis characterizing ellipsoidal reflector 20 may be, for example, about 12 mm to about 30 mm. The length of the major axis may typically be about 20 mm, for example. The length of the minor axis characterizing ellipsoidal reflector 20 may be, for example, about 10 mm to about 20 mm. The length of the minor axis may typically be about 13 mm, for example.

The ellipsoidal reflector may collect light from flow channel 30 over a range of angles corresponding to a numerical aperture that may be, for example, $\geq 1.0$, $\geq 1.1$, $\geq 1.2$, $\geq 1.3$, $\geq 1.4$, or $\geq 1.5$. This collection numerical aperture may be, for example, about 1.0 to about 1.5. The collection numerical aperture may typically be about 1.3, for example.

As noted above spherical reflector 25 has a radius of curvature $R_c$ that is equal or approximately equal to the distance between the conjugate foci of ellipsoidal reflector 20. The value of $R_c$ may be, for example, about 5 mm to about 20 mm.

The numerical aperture of spherical reflector 25 for collection of light from flow channel 30 typically matches the numerical aperture for collection by ellipsoidal reflector 20. The typical numerical aperture for spherical reflector 25 may thus be about 1.3, for example, as is the case for ellipsoidal reflector 20.

The spherical reflector typically approximately doubles the amount of light collected from flow channel 30. The effective numerical aperture for collection by the ellipsoidal and spherical reflectors in combination is therefore approximately the square root of two times the NA of the ellipsoidal reflector. The effective numerical aperture for collection by the ellipsoidal and spherical reflectors in combination may typically be about 1.8, for example. Use of the spherical reflector in combination with the ellipsoidal reflector may therefor further improve the sensitivity with which particles or particle characteristics are detected, or facilitate the use of lower sensitivity detectors in place of PMTs.

Referring again to FIG. 2, the excitation beams enter flow cell 15 through one flat face of central block 32, pass through flow channel 30, and exit flow cell 15 through a second flat face of central block 32 on the opposite side from the entry face. Optionally, forward scattered excitation tight may be collected and detected after it passes through the exit face. Such forward scattered excitation light may be separated from the excitation beams passing through the exit face with spatial fillers, for example.

Side scattered excitation light may also be optionally collected and detected. In the illustrated example, ellipsoidal reflector 20 comprises a gap in its reflective coating that allows excitation light that is scattered orthogonally to the axis of the excitation beam to exit flow cell 15. This gap may have, for example, the shape of a slit (a long and narrow window) oriented parallel to flow channel 30. Such a slit-shaped gap may provide, for example, collection of scattered light with a cone ½ angle along the length of the slit of $\leq$about 60 degrees. The typical cone ½ angle along the length of the slit may be for example about 50 degrees. The cone ½ angle perpendicular to the length of the slit may be, for example, $\leq$about 10 degrees, and may typically be $\leq$about 5 degrees. Such a slit arrangement may allow efficient collection of side-scattered excitation light without significantly reducing the collection of fluorescence. Other shapes for the gap may also be used if suitable.

Alternatively, the reflective coating on the ellipsoidal reflector, or a portion of the reflective coating, may be selected to be reflective (e.g., highly reflective) at fluorescence wavelengths but transmissive (e.g., highly transmissive) at the wavelengths of one or more of the excitation beams. For example, the coating may be selected to be highly transmissive at the wavelengths of the central excitation beam, which is incident on channel 30 at or near zero degrees angle of incidence. Such a coating that is highly reflective for fluorescence but transmissive or highly transmissive for scattered excitation light may be used, for example, on the entire reflective surface of ellipsoidal reflector 20, or on only a portion of the reflector corresponding to the gap in the reflective coating shown in FIG. 2 and described above. This arrangement may provide side scattering collection cone ½ angles as described above for the "gap" variation without reducing the collection of fluorescence.

As another alternative, the reflective coating on ellipsoidal reflector 20 may be selected to be highly reflective for fluorescence and also highly reflective for one or more of the excitation beams. Side scattered excitation light is then collected by ellipsoidal reflector 20 and focused at or near F2, where it may be coupled into an optical fiber along with the collected fluorescence. The collected side-scattered excitation light may be subsequently separated from the fluorescence and detected in the detection module using, for example, an additional filter arrangement and detector configured similarly to those described above for fluorescence detection. This arrangement may also provide efficient collection of side-scattered light without significantly reducing fluorescence collection.

The reflective coating on spherical reflector 25 may optionally be selected to be highly reflective for one or more of the excitation beams as well as for the fluorescence. In this case the spherical collector collects additional side-scattered excitation light (scattered away from the elliptical reflector) and retro-reflects it back through the flow channel toward the elliptical reflector. This arrangement may be used with any of the side-scattering collection implementations described above to improve the collection of side-scattered excitation light, and may increase the sensitivity with which the particle analyzer detects particles, or particle characteristics, from the side-scattered light.

Flow cell 15 may be assembled, for example, from four separately made solid portions that are bonded together: an ellipsoidal reflector portion, a central block portion having a surface into which flow channel 30 (or a portion of flow channel 30) has been formed, a second central block portion having a surface that completes the cross-sectional contour of flow channel 30, and a spherical reflector portion. The separate pieces may be made from fused silica or another optical glass, for example, and fusion bonded to each other with pressure and heat. Alternatively, the separate pieces may be bonded to each other with an optical adhesive. Flow cell 15 may be instead assembled from any other suitable arrangement of subcomponents, or by any other suitable method.

The one or more optical fibers 50 may, for example, be glued to flow cell 15 with an optical adhesive. Any other suitable method of coupling optical fibers 50 to flow cell 15 may also be used. Any suitable conventional optical fibers may be used.

The use of a flow cell having integrated reflectors as described herein reduces the susceptibility of the particle analyzer to misalignment. For example, the locations of F1, F2, the center of curvature of the spherical reflector, and the flow channel are fixed in position in the integrated flow cells described herein, so their relative positions will not be significantly affected by vibration, thermal cycling or other environmental factors tending to misalign optical instruments. Using an optical fiber (or fibers) bonded to the flow cell to transmit collected light to the detector modules further reduces the susceptibility of the particle analyzer to misalignment for the same reasons.

FIGS. 3A-3G show various views of flow cell 15 by which its dimensions may be better understood. Note that although FIGS. 1A-1B, 2, and 3A-3G show the central block portion 32 of flow cell 15 to have an elongated rectangular cross-section perpendicular to the major axis of the ellipsoidal reflector, this cross section may instead be for example square or approximately square with side lengths approximately equal to or greater than the diameter of the attached spherical reflector portion of the flow cell.

Referring now particularly to FIGS. 3A-3G, thickness T1 of central block portion 32 of the flow cell measured parallel to the major axis of the elliptical reflector may be, for example, about 2 mm to about 5 mm, and may typically be for example about 2 mm to about 3 mm. Width W1 of central block portion 32 measured parallel to a minor axis of the elliptical reflector and perpendicular to the flow channel may be, for example, about 10 mm to about 25 mm, or about 10 mm to about 50 mm, and may typically be for example about 20 mm. Height H1 of central block portion 32 measured parallel to the flow channel may also be for, example, about 10 mm to about 25 mm, or about 10 mm to about 50 mm, and may typically be for example about 20 mm. The diameter D1 of the spherical reflector where it attaches to the central block portion may be, for example, about 10 mm to about 25 mm or about 10 mm to about 50 mm. The diameter D2 of the elliptical reflector where it attaches to the central block portion may be, for example, about 5 mm to about 25 mm.

The largest dimension of flow cell 15 measured along any direction may be, for example, about 25 mm to about 50 mm.

Figure 4:
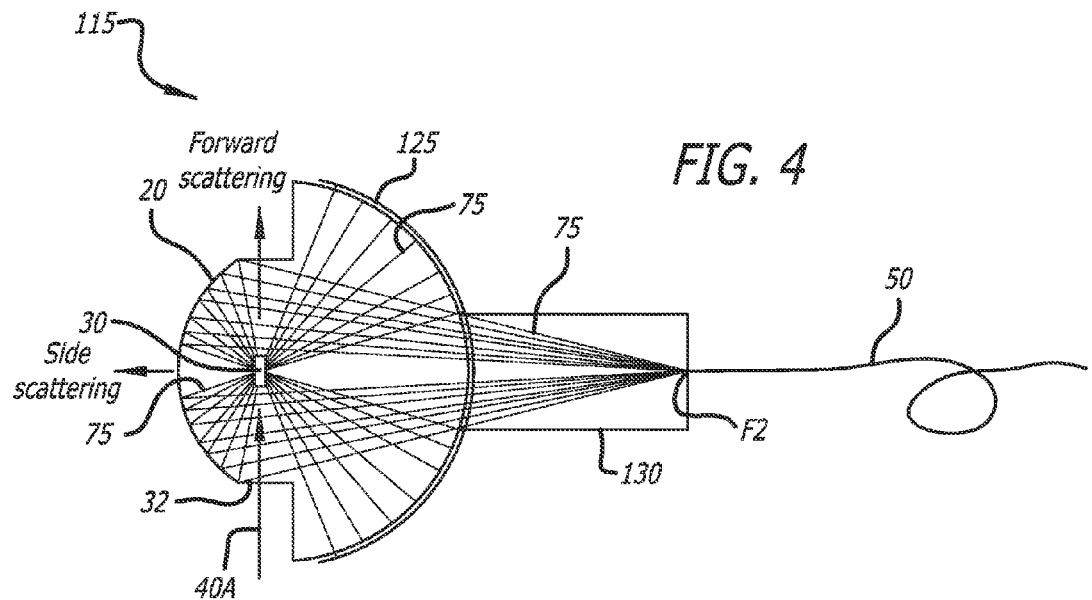
FIG. 4 schematically illustrates a cross-sectional view of another example flow cell comprising integrated ellipsoidal and spherical reflectors that may be employed in the flow cytometer of FIGS. 1A-1B.

FIG. 4 illustrates a flow cell 115 that may be substituted for flow cell 15 in the particle analyzers disclosed herein. Flow cell 115 includes ellipsoidal reflector 20 and central block portion 32 as in flow cell 15 described above. Flow cell 115 also includes a spherical reflector 125 arranged and functioning similarly to that in flow cell 15 with its center of curvature located at or approximately at F1 in flow channel 30, except that the radius of curvature of spherical reflector 125 is smaller than the distance between the conjugate foci of ellipsoidal reflector 20. As a consequence, F2 is located behind spherical reflector 125 along the major axis of the ellipsoidal reflector. Compared to flow cell 15, flow cell 115 includes an additional portion 130 extending along the major axis of the ellipsoidal reflector from spherical reflector 125 to an end surface located at or approximately at F2. Spherical reflector 125 has an unreflective central portion centered on the major axis of ellipsoidal reflector 20 sized to allow the cone of light focused by the ellipsoidal reflector to enter extending portion 130 to reach F2. The central unreflective portion of spherical reflector 125 may have a circular shape, for example. Light focused to F2 may be coupled into one or more optical fibers 50 coupled (e.g., bonded) to extending portion 130 at or near F2.

The dimensions and other parameters of ellipsoidal reflector 20 and central block portion 32 in flow cell 115 may be, for example, the same as those provided above for flow cell 15.

The radius of curvature $R_c$ of spherical reflector 125 in flow cell 115 may be, for example, about 5 mm to about 20 mm, and may typically be about 8 mm for example. The numerical aperture and corresponding cone angle for collection of light from flow channel 30 by spherical reflector 125 may generally be the same as for spherical reflector 25 in flow cell 15, except that as described above a central portion of reflector 125 is unreflective and thus does not collect light. The cone ½ angle of light not collected by the spherical reflector from flow channel 30 may be for example ≤about 30 degrees, and may typically be about 5 degrees, for example. This cone ½ angle depends on the difference between the radius of curvature of the spherical reflector and the distance between the conjugate foci of the ellipsoidal reflector, which is also approximately the length of extending portion 130.

Extending portion 130 of flow cell 115 may have a square or circular cross-section perpendicular to the major axis of the ellipsoidal reflector, for example, and thus a rectangular or cylindrical shape. The smallest dimension of extending portion 130 perpendicular to the major axis of the ellipsoidal reflector at the joint between extending portion 130 and spherical reflector 125 may be selected to be sufficiently large to allow the cone of light focused by the ellipsoidal reflector to F2 to enter extending portion 130 unobstructed. The length of extending portion 130 may be, for example, ≤about 20 mm, and may typically be 10 mm for example. The width or diameter of extending portion 130 may be, for example, about 1 mm to about 5 mm, and may typically be about 3 mm, for example.

Forward and side scattered light may be collected and detected from flow cell 115 in the same manner as described above for flow cell 15.

Flow cell 115 may be assembled by fusion bonding separate components similarly as to described above with respect to flow cell 15. Any other suitable manufacturing method may also be used. The components of flow cell 115 may be made from fused silica or other optical glasses, for example.

As in flow cell 15, the one or more optical fibers 50 may, for example, be glued to flow cell 115 with an optical adhesive. Any other suitable method of coupling optical fibers 50 to flow cell 115 may also be used. Any suitable conventional optical fibers may be used.

The largest dimension of flow cell 115 measured along any direction may be, for example, about 12 mm to about 25 mm, and may be for example smaller than that for flow cell 15 because flow cell 115 may use a smaller radius of curvature spherical reflector.

Flow cell 115 may provide the advantages described above with respect to flow cell 15. In addition, for the same size and shape of ellipsoidal reflector flow cell 115 may be more compact than flow cell 15 because flow cell 115 employs a smaller radius of curvature spherical reflector. This may facilitate integration of the flow cell into a particle analyzer.

Figure 5:
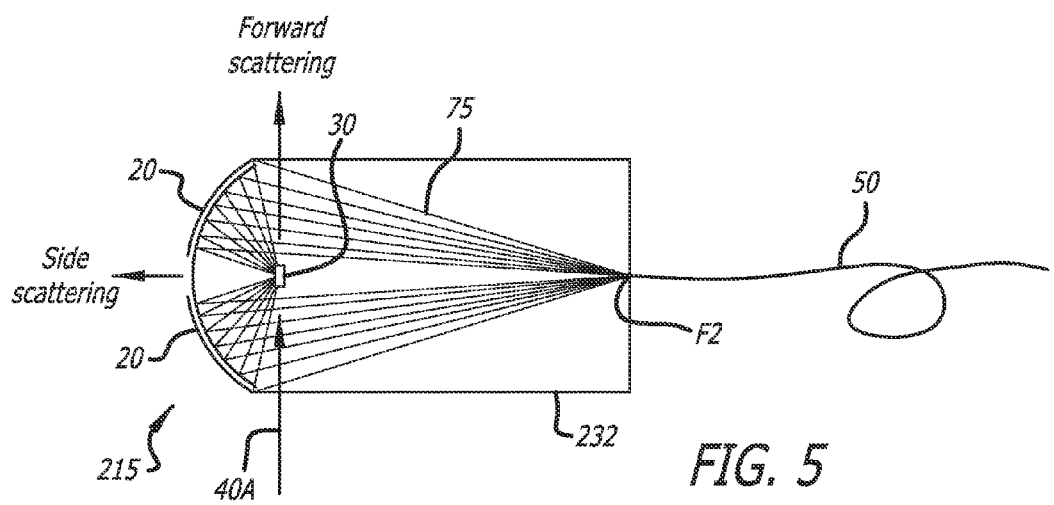
FIG. 5 schematically illustrates a cross-sectional view of another example flow cell comprising an integrated ellipsoidal reflector that may be employed in the flow cytometer of FIGS. 1A-1B.

FIG. 5 illustrates another flow cell 215 that may be substituted for flow cell 15 in the particle analyzers disclosed herein. Flow cell 215 includes an ellipsoidal reflector 20 and a block 232 comprising a flow channel 30, but lacks the spherical reflector of the flow cells described above. In flow cell 215 ellipsoidal reflector 20 and channel 30 are arranged and function as in the previously disclosed flow cells. Block 232 differs from central block 32 in the previously described flow cells primarily in that block 232 extends along the major axis of the ellipsoidal reflector to an end surface located at or approximately at F2. Light focused to F2 may be coupled into one or more optical fibers 50 coupled (e.g., bonded) to block 232 at or near F2.

The dimensions and other parameters of ellipsoidal reflector 20 may be, for example, the same as those provided above for flow cell 15. Block 232 may have a square or circular cross-section perpendicular to the major axis of the ellipsoidal reflector, for example, and thus a rectangular or cylindrical shape. The width or diameter of block 232 perpendicular to the major axis of the ellipsoidal reflector typically matches or exceeds that of the ellipsoidal reflector. The width or diameter of block 232 may be, for example, about 3 mm to about 10 mm, and may typically be about 5 mm, for example. The length of block 232 along the major axis of the ellipsoidal reflector may be, for example, about 10 mm to about 15 mm, and/or about 5 mm to about 25 mm, and may typically be about 9 mm, for example.

Forward and side scattered light may be collected and detected from flow cell 215 in the same manner as described above for flow cell 15.

Flow cell 215 may be assembled by fusion bonding separate components similarly as to described above with respect to flow cells 15 and 115. Any other suitable manufacturing method may also be used. The components of flow cell 215 may be made from fused silica or other optical glasses, for example.

As in flow cell 15, the one or more optical fibers 50 may, for example, be glued to flow cell 215 with an optical adhesive. Any other suitable method of coupling optical fibers 50 to flow cell 115 may also be used. Any suitable conventional optical fibers may be used.

Integrated flow cell 215 may provide enhanced light collection, improved transmission of light to detectors, and reduced sensitivity to misalignment similarly as to described above with respect to flow cells 15 and 115. In comparison to these flow cells, flow cell 215 is mechanically and optically simpler and may therefore be more easily and less expensively manufactured.

The flow cells described above include integrated ellipsoidal or integrated ellipsoidal and spherical reflectors. As noted above, similar arrangements of reflectors may be used to collect scattered or emitted light from a sample stream in air, and may be useful in a sorting particle analyzer, for example. FIG. 6 schematically illustrates a top view of such an arrangement. In the illustrated particle analyzer 210, a nozzle or other suitable mechanism (not shown) produces a sample stream 230 in air (that is, not enclosed in a flow cell). The optical arrangement in this example is analogous to that of particle analyzer 10 with flow cell 15. An ellipsoidal reflector 220 is positioned with its nearest focus F1 in sample stream 230, among the excitation volumes defined by the intersection of the excitation light beams with the sample stream, and with its other focus F2 at or approximately at the surface of a spherical reflector 225. The center of curvature of spherical reflector 225 is at or approximately at F1. This arrangement functions as described above with respect to flow cell 15 to efficiently collect and couple light into one or more optical fibers 50 for transmission to detection module 55. In another variation, analogous to the use of flow cell 115 described above, the spherical reflector may have a radius of curvature smaller than the distance between the conjugate foci of the ellipsoidal reflector. In such a case, the ellipsoidal reflector may focus light to F2 through, for example, an unreflective portion of spherical reflector 225, or through a physical gap (hole spherical reflector 225. In yet another variation, analogous to the use of flow cell 215 described above, the ellipsoidal reflector may be used without the spherical reflector.

As noted above, the particle analyzers illustrated in FIGS. 1A-1B and 6 employ, in addition to ellipsoidal and spherical reflectors, refractive beam steering optic 45 that allows multiple closely spaced excitation beams to be directed into the sample stream at low angles of incidence. These low angles of incidence may be, for example, less than or equal to about 1 degree. As explained above, the low angles of incidence may result in lower noise and higher detection sensitivity for light scattered or emitted by particles in the sample stream.

Figure 7:
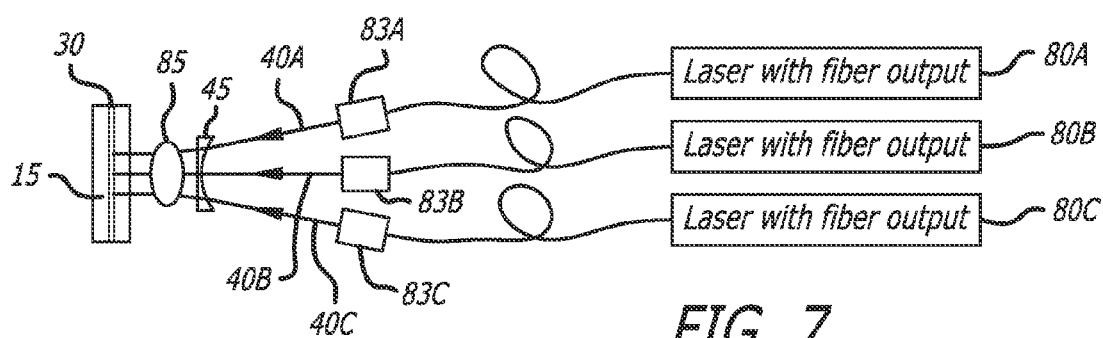
FIG. 7 schematically illustrates the use of a wedge lens comprising wedge portions symmetrically arranged around a central flat as a refractive beam steering optic to direct multiple closely spaced excitation laser beams into the flow cell of a flow cytometer at low angles of incidence on the flow stream.

The general operation of beam steering optic 45, and the design of one example beam steering optic, may be appreciated by reference to FIG. 7 and FIGS. 8A-8D. In FIG. 7, the combinations of lasers 80A-80C and fiber collimators 83A-83C correspond to light source modules 35A-35C shown in FIG. 1B. Collimators 83A and 83C direct the outermost excitation beams (40A and 40C) along paths that would result in relatively large angles of incidence on flow channel 30 in the absence of refractive beat steering optic 45. Without refractive beam steering optic 45, the minimum angles of incidence on the flow channel for the outer excitation beams are determined by the closest possible spacing of the fiber collimators and the distance between the collimators and the flow channel. Refractive beam steering optics 45 as disclosed herein may relax these constraints, and allow low angles of incidence on flow channel 30 to be achieved with excitation beams that are output from fiber collimators (or other light sources) that are spaced apart from each other. This may facilitate modifying or replacing light sources without significantly affecting optical alignment of the particle analyzer.

In the example illustrated in FIG. 7 and FIGS. 8A-8D, refractive beam steering optic 45 is a single integrated optical element comprising optical wedge portions 90 symmetrically arranged around a flat portion 95. The central excitation beam 40B passes undeflected through flat portion 95. The outer two excitation beams pass through corresponding outer wedge portions 90, which deflect the two outer beams away from each other to redirect them toward flow channel 30 at reduced angles of incidence. If more than three excitation beams are employed, the refractive beam steering optic 45 may optionally include additional wedge portions arranged around the central flat portion to deflect the additional excitation beams, similarly to as just described, to reduce their angles of incidence on flow channel 30.

Referring now particularly to FIGS. 8A-8D, wedge angle a of wedge portions 90 may be, for example, about 5 degrees to about 10 degrees, and may typically be about 5.7 degrees, for example. The narrow ends of wedge portions 90 point toward the central flat portion 95. Thickness L1 of central flat portion 95 may be, for example, about 1 mm to about 2 mm, and may typically be about 1.2 mm, for example. Widths L2 and L3 of the wedge portions and the central flat portion respectively, and their height L4, are typically selected to be about 1 diameter or about 2 diameters of the incident excitation beams. Widths L2 and L3 may be identical or substantially identical, for example, but are not necessarily so. Widths L2 and L3 may be, for example, about 1 mm to about 5 mm, and may typically be about 2 mm, for example. Height L4 may be, for example, about 3 mm to about 15 mm, and may typically be about 5 mm, for example.

The example refractive beam steering optic illustrated in FIG. 7 and FIGS. 8A--8D may be formed as a molded lens, for example, and may be formed for example from fused silica or another optical glass. Any other suitable manufacturing methods and materials may also be used.

Referring now to FIG. 9, refractive beam steering optic 45 may alternatively be implemented as two separate optical wedges symmetrically arranged around a central air gap with their narrow ends pointing into the gap. This arrangement functions similarly to that of FIG. 7. The central excitation beam 40B passes undeflected through the air gap. The outer two excitation beams pass through corresponding wedges, which deflect the two outer beams away from each other to redirect them toward flow channel 30 at reduced angles of incidence. If more than three excitation beams are employed, the refractive beam steering optic 45 may optionally include additional wedges arranged around the central air gap to deflect the additional excitation beams, similarly to as just described, to reduce their angles of incidence on flow channel 30. Analogously to the implementation of FIG. 7, the wedge angles may be, for example, about 5 degrees to about 10 degrees, and may typically be about 5.7 degrees, for example. The wedges may have a length in the direction from their thick to their thin ends (corresponding to L2 in FIGS. 8A-8D) of, for example, about 1 mm to about 5 mm. The wedges may have a height (corresponding to L4 in FIGS. 8A-8D) of, for example, about 1 mm to about 5 mm. The wedges may have a thickness at their thickest end of, for example, about 1 mm to about 5 mm. The air gap between the wedges may have a width (corresponding to L3 in FIGS. 8A-8D) of, for example, about 1 mm to about 5 mm.

The wedges used in this implementation may be formed, for example, from fused silica or another optical glass. Any suitable manufacturing method and material may be used.

Referring now to FIG. 10, refractive beam steering optic 45 may alternatively be implemented as a diverging lens, such as a diverging cylindrical lens for example. The diverging lens may have a focal length of, for example, about −5 mm to about −50 mm.

The wedge angle of the wedges used FIG. 9, or of the wedge portions of the implementation shown in FIG. 7 and FIG. 8A-8D, may be selected to be sufficiently small that the deflection of the excitation beams is not sensitive to wavelength. The deflection of the excitation beams by a diverging cylindrical lens may be made similarly insensitive to wavelength by, for example, choice of focal length and of lens material. Such insensitivity to wavelength may further facilitate modifying or replacing light sources (e.g., changing wavelengths) without significantly affecting the optical alignment of the particle analyzer.

As an alternative to beam steering optic 45, an arrangement of two or more dichroic mirrors may be used to direct the excitation beams to the sample stream. Such an arrangement may be complex, bulky, and susceptible to misalignment, however. As another alternative, a dispersion prism or dispersion grating may be used to deflect excitation beams of different wavelength in the same direction to reduce the angles between them, and thereby reduce their angles of incidence on the sample stream. (This approach may be understood as basically the reverse of a prism or grating separating light into different colors). However, the high wavelength sensitivity on which this approach is based may make it difficult to modify or replace light sources without significantly affecting optical alignment.

Referring again to FIGS. 7, 9, and 10, in the illustrated examples the excitation beams deflected by refractive beam steering optic 45 are incident on an optional beam shaper 85. As described above with respect to FIGS. 1A-1B, beam shaper 85 (if present) typically focuses the excitation beams to elliptically shaped beam waists at channel 30, with the beam waists' minor axes oriented parallel to the channel and their major axes oriented perpendicular to the channel. Optionally, beam shaper 85 may be configured to provide elliptically shaped beam waists with other desirable orientations of their major and minor axes, or to provide other desirable beam waist shapes and orientations. Beam shaper 85 may comprise, for example, a pair of crossed cylindrical lenses selected for example based on the shape, diameter, and divergence of the input excitation beams and on the desired waist shape and diameter of the excitation beams at their focus in flow channel 30. Beam shaper 85 may be positioned between refractive beam steering optic 45 and flow cell 15 as shown in FIGS. 7, 9, 10, and if so may be integrated with (e.g., fixed onto) the flow cell as shown in FIG. 11D. Alternatively, beam shaper 85 may be placed in front of refractive beam steering optic 45 as shown in FIG. 11B and FIG. 11C. FIG. 11C shows the beam shaper integrated with (e.g., fixed onto) the flow cell. Alternatively, the refractive beam steering optic may be integrated into the beam shaper by, for example, inserting the refractive beam steering optic between crossed cylindrical lenses in the beam shaper as shown schematically in FIG. 11A. In such cases, the assembly may be further integrated with (e.g., fixed onto) the flow cell as shown in FIG. 11E.

Referring again to FIG. 7, the fiber collimators, the refractive beam steering optic 45, and the beam shaper may optionally be mounted on a common base-plate or other support structure (not shown) made from materials of low thermal expansion to provide a high level of alignment stability. Suitable materials for such a common support structure may include, for example, low-thermal expansion coefficient borosilicate glasses, fused silica, and machinable ceramics.

This disclosure is illustrative and not limiting. Further modifications will be apparent to one skilled in the art in light of this disclosure and are intended to fall within the scope of the appended claims.

What is claimed is:

1. A particle analyzer comprising:
an ellipsoidal reflector having a shape characterized by lengths of major and minor axes of a defining ellipse and having conjugate foci F1 and F2 located on the major axis, with F1 in a flow path for a stream of particles;
one or more light sources configured to provide one or more excitation light beams directed to intersect the stream of particles at or approximately at F1, thereby exciting fluorescence from the particles; and
a spherical reflector having its center of curvature coincident or approximately coincident with F1;
wherein at least a portion of fluorescence emitted toward the ellipsoidal reflector is focused by the ellipsoidal reflector to one or more locations at or near F2, at least a portion of fluorescence emitted toward the spherical reflector is retro-reflected by the spherical reflector toward the ellipsoidal reflector which focuses the retro-reflected fluorescence to the one or more locations at or near F2, and the ratio of the major and minor axes of the ellipse defining the shape of the ellipsoidal reflector is greater than or equal to about 1.2.

2. The particle analyzer of claim 1, wherein the radius of curvature of the spherical reflector is equal or approximately equal to the distance between F1 and F2.

3. The particle analyzer of claim 1, wherein the radius of curvature of the spherical reflector is less than the distance between F1 and F2, and the ellipsoidal reflector focuses fluorescence incident on it through the spherical reflector to F2 beyond the spherical reflector.

4. The particle analyzer of claim 1, wherein the numerical aperture of the spherical reflector for collection of fluorescence emitted toward it, retro-reflected to the ellipsoidal reflector, and focused to F2 is the same or approximately the same as the numerical aperture of the ellipsoidal reflector for collection of fluorescence emitted toward it.

5. The particle analyzer of claim 1, comprising an optical fiber into which fluorescence focused to one or more of the locations at or near F2 is coupled.

6. The particle analyzer of claim 5, wherein the ratio of the lengths of the major and minor axes of the defining ellipse provides an ellipsoidal reflector shape that matches or approximately matches the fluorescence focused to locations at or near F2 to a numerical aperture characterizing the optical fiber.

7. The particle analyzer of claim 1, comprising a flow cell formed from a material transparent or substantially transparent to light at wavelengths of the excitation beam and wavelengths of the fluorescence and having a flow channel accommodating flow of the stream of particles along the flow path, wherein the ellipsoidal and spherical reflectors are integral parts of the flow cell formed by reflective coatings on outer surfaces of the flow cell.

8. The particle analyzer of claim 7, wherein except for the flow channel all interior portions of the flow cell are solid and formed from the transparent or substantially transparent material.

9. The particle analyzer of claim 7, wherein the flow cell comprises a central block portion between the ellipsoidal and spherical reflectors, the central block portion including the flow channel and also including a flat entrance surface through which the one or more excitation beams enter the flow cell and an opposing flat exit surface through which the one or more excitation beams exit the flow cell.

10. The particle analyzer of claim 7, wherein the radius of curvature of the spherical reflector is less than the distance between F1 and F2, and the ellipsoidal reflector focuses fluorescence incident on it through the spherical reflector to F2 beyond the spherical reflector.

11. The particle analyzer of claim 10, wherein the flow cell comprises:
a central block portion between the ellipsoidal and spherical reflectors, the central block portion including the flow channel and also including a flat entrance surface through which the one or more excitation beams enter the flow cell and an opposing flat exit surface through which the one or more excitation beams exit the flow cell; and
a portion extending along the major axis beyond the spherical reflector to an end surface at or approximately at F2.

12. The particle analyzer of claim 1, wherein the ellipsoidal reflector comprises a narrow elongated window through which light from the one or more excitation light beams side-scattered by the particles may pass.

13. The particle analyzer of claim 1, further comprising:
a flow cell comprising a flow channel accommodating flow of the stream of particles; and
one or more optical fibers bonded to the end surface of the flow cell at or approximately at F2,
wherein the ellipsoidal reflector is formed as an integral part of the flow cell by a reflective coating on an exterior surface of the flow cell with F1 in the flow channel, the flow cell extending along the major axis of the defining ellipse to an end surface at or approximately at F2,
wherein the fluorescence focused by the ellipsoidal reflector to the one or more locations at or near F2 is coupled into the one or more optical fibers, and the ratio of the lengths of the major and minor axes of the defining ellipse provide an ellipsoidal reflector shape that matches the fluorescence focused to the one or more locations at or near F2 to a numerical aperture characterizing the one or more optical fibers.

14. The particle analyzer of claim 13, wherein the numerical aperture of the ellipsoidal reflector for collection of fluorescence emitted toward it is greater than or equal to about 1.3, and wherein the fluorescence focused by the ellipsoidal reflector has a cone half angle not exceeding a numerical aperture of the one or more optical fibers of about 0.2 to about 0.5 at the one or more locations at or near F2.

15. The particle analyzer of claim 13, wherein the one or more light sources includes three or more excitation light sources each providing an excitation beam of light, the particle analyzer further comprising:
a refractive beam steering optic which directs the three or more excitation beams to intersect the sample stream at corresponding separate and spaced-apart locations along the sample stream; and
wherein excitation beams passing through opposite outer portions of the refractive beam steering optic are deflected away from each other to thereby reduce their angles of incidence on the sample stream.

16. The particle analyzer of claim 15, wherein the refractive beam steering optic comprises two outer wedge portions arranged symmetrically around a central flat portion, at least one of the excitation beams is incident on and passes substantially undeflected through the central flat portion, and excitation beams incident on different ones of the wedge portions are deflected away from each other to redirect them toward the sample stream at reduced angles of incidence.

17. The particle analyzer of claim 15, wherein the refractive beam steering optic comprises two separate optical wedges arranged symmetrically around an air gap, at least one of the excitation beams passes undeflected through the central air gap, and excitation beams incident on different ones of the optical wedges are deflected away from each other to redirect them toward the sample stream at reduced angles of incidence.

18. The particle analyzer of claim 15, wherein the refractive beam steering optic comprises a diverging cylindrical lens, at least one of the excitation beams passes substantially undeflected through a central portion of the cylindrical lens, and excitation beams incident on opposite outer portions of the cylindrical lens are deflected away from each other to redirect them toward the sample stream at reduced angles of incidence.

19. A particle analyzer comprising:
an ellipsoidal reflector having a shape characterized by lengths of major and minor axes of a defining ellipse and having conjugate foci F1 and F2 located on the major axis, with F1 in a flow path for a stream of particles;
one or more light sources configured to provide one or more excitation light beams directed to intersect the stream of particles at or approximately at F1, thereby exciting fluorescence from the particles; and
a spherical reflector having its center of curvature coincident or approximately coincident with F1;
wherein at least a portion of fluorescence emitted toward the ellipsoidal reflector is focused by the ellipsoidal reflector to one or more locations at or near F2, at least a portion of fluorescence emitted toward the spherical reflector is retro-reflected by the spherical reflector toward the ellipsoidal reflector which focuses the retro-reflected fluorescence to the one or more locations at or near F2, the radius of curvature of the spherical reflector is less than the distance between F1 and F2, and the ellipsoidal reflector focuses fluorescence incident on it through the spherical reflector to F2 beyond the spherical reflector.

20. A particle analyzer comprising:
an ellipsoidal reflector having a shape characterized by lengths of major and minor axes of a defining ellipse and having conjugate foci F1 and F2 located on the major axis, with F1 in a flow path for a stream of particles;
one or more light sources configured to provide one or more excitation light beams directed to intersect the stream of particles at or approximately at F1, thereby exciting fluorescence from the particles; and
a spherical reflector having its center of curvature coincident or approximately coincident with F1;
wherein at least a portion of fluorescence emitted toward the ellipsoidal reflector is focused by the ellipsoidal reflector to one or more locations at or near F2, at least a portion of fluorescence emitted toward the spherical reflector is retro-reflected by the spherical reflector toward the ellipsoidal reflector which focuses the retro-reflected fluorescence to the one or more locations at or near F2, and the ratio of the major and minor axes of the ellipse defining the shape of the ellipsoidal reflector is greater than or equal to about 1.4.

* * * * *